United States Patent
Higashi et al.

(10) Patent No.: US 11,827,594 B2
(45) Date of Patent: *Nov. 28, 2023

(54) FLUORINATED ORGANIC COMPOUND PRODUCTION METHOD

(71) Applicants: DAIKIN INDUSTRIES, LTD., Osaka (JP); SAGA UNIVERSITY, Saga (JP)

(72) Inventors: Masahiro Higashi, Osaka (JP); Yosuke Kishikawa, Osaka (JP); Tsugio Kitamura, Saga (JP)

(73) Assignees: DAIKIN INDUSTRIES, LTD., Osaka (JP); SAGA UNIVERSITY, Saga (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/041,731

(22) PCT Filed: Mar. 29, 2019

(86) PCT No.: PCT/JP2019/014277
§ 371 (c)(1),
(2) Date: Sep. 25, 2020

(87) PCT Pub. No.: WO2019/189861
PCT Pub. Date: Oct. 3, 2019

(65) Prior Publication Data
US 2021/0114966 A1    Apr. 22, 2021

(30) Foreign Application Priority Data

Mar. 30, 2018 (JP) ................. 2018-067377

(51) Int. Cl.
*C07C 67/307* (2006.01)
(52) U.S. Cl.
CPC ................. *C07C 67/307* (2013.01)
(58) Field of Classification Search
CPC ..... C07C 67/307; C07C 69/738; C07C 17/02; C07C 231/12; C07C 45/63; C07C 47/14; C07C 51/363; C07C 51/62; C07C 69/62; A61K 35/74; A61K 9/00; A61K 9/0014; A61P 17/02; A61P 1/02; A61P 31/00; A61P 31/12; A61P 31/22; A61P 35/00; A61P 31/20; C12N 1/20; C12N 1/205; C12P 1/04; C12R 2001/01; C12Y 304/00; C08G 18/161; C08G 18/18; C08G 18/22; C08G 18/4018; C08G 18/7671; C08J 9/0038; C08J 9/0066; C08J 9/0085; C08J 9/12; C08J 9/125; C08J 9/142; Y02A 50/30

See application file for complete search history.

(56) References Cited

FOREIGN PATENT DOCUMENTS

JP    2015-157788    9/2015

OTHER PUBLICATIONS

Kitamura et al. (A Practical and Convenient Fluorination of 1,3-Dicarbonyl Compounds Using Aqueous HF in the Presence of Iodosylbenzene, Organic Letters, vol. 13, No. 9, pp. 2392-2394, Published 2011) (Year: 2011).*
Togo et al. (Polymer-Supported Hypervalent Iodine Reagents, Synlett, No. 12, pp. 1966-1975, Published 2002) (Year: 2002).*
Kitamura et al. 2015 (Hypervalent Iodine-Mediated Fluorination of Styrene Derivatives: Stoichiometric and Catalytic Transformation to 2,2-Difluoroethylarenes, J. Org, Chem, 80, pp. 10431-10436, Published 2015) (Year: 2015).*
Kitamura et al. 2012 (Reactions of Iodonium Ylides of 1,3-Dicarbonyl Compounds with HF Reagents, Molecules, 17, pp. 6625-6632, Published 2012). (Year: 2012).*
Togo et al., "Synthetic Use of Poly [4-(diacetoxyiodo)styrene] for Organic Reactions", Bull. Chem. Soc. Jpn., 1999, vol. 72, pp. 2351-2356.
International Search Report dated Jun. 18, 2019 in International (PCT) Application No. PCT/JP2019/014277.
Kitamura et al., "A Practical and Convenient Fluorination of 1,3-Dicarbonyl Compounds Using Aqueous HF in the Presence of Iodosylbenzene", Organic Letters, 2011, vol. 13, No. 9, pp. 2392-2394.
Kitamura et al., "Facile Synthesis of-2-Fluoro-1,3-dicarbonyl Compounds With Aqueous Hydrofluoric Acid Mediated by Iodosylarenes", Synthesis, 2013, vol. 45, No. 22, pp. 3125-3130.
Kitamura et al., "A Convenient Synthesis of 2-Fluoro- and 2-Chloromalonic Esters Mediated by Hypervalent Iodine", Synthesis, 2015, vol. 47, No. 20, pp. 3241-3245.
Nash et al., "Apparent Electrophilic Fluorination of 1,3-Dicarbonyl Compounds Using Nucleophilic Fluoride Mediated by PhI(OAc)$_2$,", European Journal of Organic Chemistry, 2015, vol. 2015, No. 17, pp. 3779-3786.

(Continued)

*Primary Examiner* — Yevgeny Valenrod
*Assistant Examiner* — Blaine G Doletski
(74) *Attorney, Agent, or Firm* — Wenderoth, Lind & Ponack, L.L.P.

(57) ABSTRACT

An object of the present invention is to provide a method for producing a fluorinated organic compound, whereby an iodosylbenzene derivative can be easily separated and recovered. The above object can be achieved by a method for producing a fluorinated organic compound, comprising step A of fluorinating an organic compound (1) by reaction with a fluorine source (3) in the presence of an iodine-containing polymer (2$ap$) having one or more hypervalent iodine aromatic ring moieties, in the presence of a combination of an oxidant (2$bo$) and an iodine-containing polymer (2$bp$) having one or more iodine aromatic ring moieties, or in the presence of an iodine-containing polymer (2$cp$) having one or more IF$_2$-substituted aromatic ring moieties; wherein the fluorine source (3) is a fluorine source (3$a$) represented by formula: MF$_n$, wherein M is H, a metal of Group 1 of the periodic table, or a metal of Group 2 of the periodic table; and n is 1 or 2, the polymer (2$cp$) having one or more IF$^2$-substituted aromatic ring moieties, or a combination thereof.

20 Claims, No Drawings

(56) References Cited

OTHER PUBLICATIONS

Wegeberg, Christina et al., "Reduction of hypervalent iodine by coordination to iron(III) and the crystal structures of PhIO and $PhIO_2$", Royal Society of Chemistry, Dalton Transactions, vol. 45, 2016, pp. 17714-17722.

Richter, Helen et al., "Preparation and Structure of a Solid-State Hypervalent-Iodine Polymer Containing Iodine and Oxygen Atoms in Fused 12-Atom Hexagonal Rings", Inorganic Chemistry, vol. 46, 2007, pp. 5555-5561.

Extended European Search Report dated Feb. 2, 2022, in corresponding European Patent Application No. 19774411.3.

Siebert, Von Hans and Handrich, Monika, "Vibrational Spectra and Structure of Iodosyl and Iodyl Compounds," Z. anorg. allg. Chem., 1976, vol. 426, pp. 173-183, with English Abstract.

\* cited by examiner

FLUORINATED ORGANIC COMPOUND PRODUCTION METHOD

TECHNICAL FIELD

The present invention relates to a method for producing a fluorinated organic compound.

BACKGROUND ART

Fluorinated organic compounds are extremely important compounds as various chemical products, such as functional materials, pharmaceutical and agrochemical compounds, and electronic materials, as well as intermediates thereof.

As a method for producing a fluorinated organic compound, for example, PTL 1 proposes a method for producing a monofluoromalonic acid derivative, comprising reacting a malonic acid ester derivative with a hydrogen fluoride source in the presence of an iodosylbenzene derivative, or in the presence of an iodobenzene derivative and an oxidant.

CITATION LIST

Patent Literature

PTL 1: JP2015-157788A

SUMMARY OF INVENTION

Technical Problem

The present inventors found that there was room for improvement in the technique of PTL 1 in that the iodosylbenzene derivative was not separated and recovered.

An object of the present invention is to provide a method for producing a fluorinated organic compound, whereby an iodosylbenzene derivative can be easily separated and recovered.

Solution to Problem

As a result of extensive studies, the present inventors found that the above object can be achieved by a method for producing a fluorinated organic compound, comprising step A of fluorinating an organic compound (1) by reaction with a fluorine source (3)
in the presence of an iodine-containing polymer (2ap) having one or more hypervalent iodine aromatic ring moieties,
in the presence of a combination of an oxidant (2bo) and an iodine-containing polymer (2bp) having one or more iodine aromatic ring moieties, or
in the presence of an iodine-containing polymer (2cp) having one or more $IF_2$-substituted aromatic ring moieties;
wherein the fluorine source (3) is
a fluorine source (3a) represented by formula: $MF_n$, wherein M is H, a metal of Group 1 of the periodic table, or a metal of Group 2 of the periodic table; and n is 1 or 2,
the iodine-containing polymer (2cp) having one or more $IF_2$-substituted aromatic ring moieties, or
a combination thereof.
Thus, the present invention has been completed.
The present invention includes the following aspects.

Item 1.

A method for producing a fluorinated organic compound, comprising step A of fluorinating an organic compound (1) by reaction with a fluorine source (3)
in the presence of an iodine-containing polymer (2ap) having one or more hypervalent iodine aromatic ring moieties,
in the presence of a combination of an oxidant (2bo) and an iodine-containing polymer (2bp) having one or more iodine aromatic ring moieties, or
in the presence of an iodine-containing polymer (2cp) having one or more $IF_2$-substituted aromatic ring moieties;
wherein the fluorine source (3) is
a fluorine source (3a) represented by formula: $MF_n$, wherein M is H, a metal of Group 1 of the periodic table, or a metal of Group 2 of the periodic table; and n is 1 or 2,
the iodine-containing polymer (2cp) having one or more $IF_2$-substituted aromatic ring moieties, or
a combination thereof.

Item 2.

The production method according to Item 1, wherein the organic compound (1) is a carbonyl compound having a hydrogen atom, or a compound having one or more unsaturated carbon-carbon bonds.

Item 3.

The production method according to Item 1 or 2, wherein the organic compound (1) is:
an organic compound represented by formula (1a):

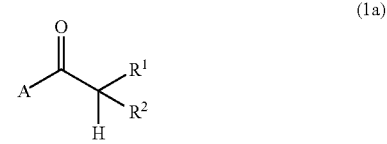

wherein
A is a hydrogen atom, an aromatic group optionally having one or more substituents, an alkyl group optionally having one or more substituents, a halogen atom, —OR, or —$NR_2$,
$R^1$ is a hydrogen atom, an organic group, or a halogen atom,
$R^2$ is a hydrogen atom, an organic group, or a halogen atom, and
R is independently at each occurrence a hydrogen atom or an organic group;
an organic compound represented by formula (1b):

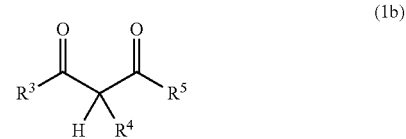

wherein
$R^3$ is a hydrogen atom, an aromatic group optionally having one or more substituents, an alkyl group optionally having one or more substituents, a halogen atom, —OR, or —$NR_2$,
$R^4$ is a hydrogen atom, an aromatic group optionally having one or more substituents, an alkyl group optionally having one or more substituents, a halogen atom, —OR, or —$NR_2$,
$R^5$ is a hydrogen atom, an aromatic group optionally having one or more substituents, an alkyl group optionally having one or more substituents, a halogen atom, —OR, or —$NR_2$, and
R is independently at each occurrence a hydrogen atom or an organic group; or an organic compound represented by formula (1c):

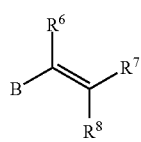

(1c)

wherein
B is an aromatic group optionally having one or more substituents, or an alkyl group optionally having one or more substituents,
$R^6$ is a hydrogen atom, an organic group, or a halogen atom,
$R^7$ is a hydrogen atom, an organic group, or a halogen atom, and
$R^8$ is a hydrogen atom, an organic group, or a halogen atom.

Item 4.

The production method according to any one of Items 1 to 3, wherein in step A, the organic compound (1) is fluorinated by reaction with the fluorine source (3) in the presence of the polymer (2ap).

Item 5.

The production method according to Item 4, wherein the polymer (2ap) having one or more hypervalent iodine aromatic ring moieties is a polymer having one or more hypervalent iodine aromatic ring moieties represented by formula (2a1):

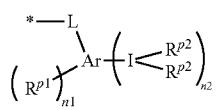

(2a1)

wherein
Ar is an aromatic ring,
$R^{p1}$ is independently at each occurrence
 an alkyl group,
 an alkoxy group,
 a group: —O—(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
 a group: —(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
 a halogen atom,
 a cyano group,
 a nitro group,
 a carboxylic acid group, or
 a sulfonic acid group;
$R^{p2}$ is independently at each occurrence
 an alkyl group,
 an alkoxy group,
 a group: —O—(CH$_2$)$_q$—NR$_3$X, wherein q is a number greater than or equal to 1; R is H or a C$_1$-C$_2$ alkyl group; and X is a halogen atom, an arylsulfonyloxy group, or an alkylsulfonyloxy group,
 a group: —(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
 a halogen atom,
 a cyano group,
 a nitro group,
 a carboxylic acid group,
 a sulfonic acid group,
 a hydroxy group, or
 a phosphoryloxy group; or
two $R^{p2}$ bonded to one iodine atom optionally together form =O;
n1 is a number greater than or equal to 0;
n2 is a number greater than or equal to 1;
the sum of n1 and n2 is in the range of 1 to 11;
L is a bond or a linker; and
* is a binding site.

Item 6.

The production method according to Item 5, wherein Ar is a benzene ring.

Item 7.

The production method according to Item 5 or 6, wherein $R^{p1}$ is independently at each occurrence an alkyl group, an alkoxy group, or a halogen atom.

Item 8.

The production method according to any one of Items 5 to 7, wherein $R^{p2}$ is independently at each occurrence a halogen atom, an acetic acid group, a trifluoroacetic acid group, a tosic acid group, a hydroxy group, a phosphoryloxy group, a trifluoromethanesulfonic acid group, a propionic acid group, a 3,3,3-trifluoropropionic acid group, a perfluoropropionic acid group, a perfluorobutyric acid group, or a methanesulfonic acid group.

Item 9.

The production method according to any one of Items 4 to 8, wherein the polymer (2ap) contains 1 mass % or more of the moiety represented by formula (2ap1), and has a mass average molecular weight in the range of 500 to 1000000.

Item 10.

The production method according to any one of Items 1 to 3, wherein in step A, the organic compound (1) is fluorinated by reaction with the fluorine source (3) in the presence of a combination of the polymer (2bp) and the oxidant (2bo).

Item 11.

The production method according to Item 10, wherein the polymer (2bp) having one or more iodine aromatic ring moieties is a polymer having one or more iodine aromatic ring moieties represented by formula (2bp1):

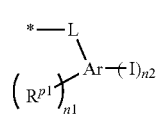

(2bp1)

wherein
Ar is an aromatic ring;
$R^{P1}$ is independently at each occurrence
 an alkyl group,
 an alkoxy group,
 a group: —O—(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
 a group: —(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group, a halogen atom,
a cyano group,
a nitro group,
a carboxylic acid group, or
a sulfonic acid group;
n1 is a number greater than or equal to 0;
n2 is a number greater than or equal to 1;
the sum of n1 and n2 is in the range of 1 to 11;
L is a bond or a linker; and
* is the binding site.

Item 12.

The production method according to Item 11, wherein Ar is a benzene ring.

Item 13.

The method according to Item 11 or 12, wherein $R^{P1}$ is independently at each occurrence an alkyl group, an alkoxy group, or a halogen atom.

Item 14.

The production method according to any one of Items 10 to 13, wherein the polymer (2bp) contains 1 mass % or more of the moiety represented by formula (2bp1), and has a mass average molecular weight in the range of 500 to 1000000.

Item 15.

The production method according to any one of Items 10 to 14, wherein the oxidant (2bo) is one or more members selected from the group consisting of:

(i) a compound represented by formula: $R^X$COOOM, wherein
$R^X$ is a hydrocarbon group optionally having one or more substituents, and
M is a hydrogen atom or a metal atom;

(ii) a compound represented by formula: $R^X$OOM, wherein
$R^X$ is a hydrogen atom or a hydrocarbon group optionally having one or more substituents, and
M is a hydrogen atom or a metal atom; and (iii) a metal oxide.

Item 16.

The production method according to Item 15, wherein the oxidant (2bo) is one or more members selected from the group consisting of metachloroperbenzoic acid, hydrogen peroxide, peracetic acid, perbenzoic acid, tert-butyl hydroperoxide, cumene hydroperoxide, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

Item 17.

The production method according to any one of Items 1 to 3, wherein in step A, the organic compound (1) is fluorinated by reaction with an iodine-containing polymer (2cp) having one or more $IF_2$-substituted aromatic ring moieties.

Item 18.

The production method according to Item 17, wherein the iodine-containing polymer (2cp) having one or more $IF_2$-substituted aromatic ring moieties is a polymer having one or more $IF_2$-substituted aromatic ring moieties represented by formula (2cp1):

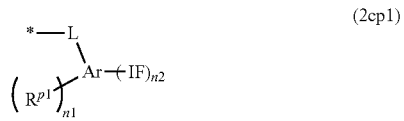

(2cp1)

wherein
Ar is an aromatic ring;
substituent $R^{p1}$ is independently at each occurrence an alkyl group, an alkoxy group, a halogen atom, a cyano group, a nitro group, a carboxylic acid group, or a sulfonic acid group;
n1 is a number greater than or equal to 0;
n2 is an integer of 1 to 5;
L is a bond or a linker; and
is a binding site.

Item 19.

The production method according to Item 18, wherein Ar is a benzene ring.

Item 20.

The method according to Item 18 or 19, wherein $R^{p1}$ is independently at each occurrence an alkyl group, an alkoxy group, or a halogen atom.

Item 21.

The production method according to any one of Items 18 to 20, wherein the iodine-containing polymer (2cp) having one or more $I_2$-substituted aromatic ring moieties contains 1 mass % or more of the moiety represented by formula (2cp1), and has a mass average molecular weight in the range of 500 to 1000000.

Item 22.

The method according to any one of Items 1 to 21, comprising step B of separating the polymer (2ap), the polymer (2bp), or the polymer (2cp) from a reaction liquid after step A is started.

Item 23.

The method according to Item 22, comprising step C of oxidizing the polymer (2ap), the polymer (2bp), or the polymer (2cp) separated from the reaction liquid in step B with an oxidant (C).

Item 24.

The production method according to Item 23, wherein the oxidant (C) is one or more members selected from the group consisting of metachloroperbenzoic acid, hydrogen peroxide, peracetic acid, perbenzoic acid, tert-butyl hydroperoxide, cumene hydroperoxide, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

Item 25.

The method according to Item 24, wherein the oxidant (C) is one or more members selected from the group consisting of metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

Advantageous Effects of Invention

The present invention provides a novel method for producing a fluorinated organic compound, whereby a compound having an iodine aromatic ring moiety can be recovered.

DESCRIPTION OF EMBODIMENTS

Term

The symbols and abbreviations in the present specification can be understood in the sense commonly used in the technical field to which the present invention pertains in the context of the present specification, unless otherwise specified.

In the present specification, the terms "comprise" and "contain" are used with the intention of including the phrases "consist essentially of" and "consist of."

Unless otherwise specified, the steps, treatments, or operations described in the present specification may be performed at room temperature.

In the present specification, room temperature can mean a temperature in the range of 10 to 40° C.

In the present specification, the phrase "$C_n$-$C_m$" (wherein n and m each represent a number) indicates that the number of carbon atoms is n or more and m or less, as a person skilled in the art would generally understand.

In the present specification, the phrase "organic compound" is understood in the ordinary sense and can be a compound having one or more carbon atoms and one or more hydrogen atoms.

In the present specification, the fluorinated organic compound refers to a compound that can be produced by fluorinating an organic compound, and may not contain a hydrogen atom.

In the present specification, unless otherwise specified, examples of the "halo (group)" may include fluoro (group), chloro (group), bromo (group), and iodine (group).

In the present specification, unless otherwise specified, examples of the "halogen (atom)" may include fluorine (atom), chlorine (atom), bromine (atom), and iodine (atom).

In the present specification, examples of the "aromatic ring" include aromatic carbon rings and aromatic heterocyclic rings.

In the present specification, the "aromatic ring moiety" refers to a moiety or group having one or more aromatic rings.

In the present specification, unless otherwise specified, examples of the "aromatic carbon rings" include aromatic hydrocarbon rings having 6 to 14 carbon atoms, and specific examples include benzene, naphthalene, anthracene, phenanthrene, and biphenyl.

In the present specification, unless otherwise specified, examples of the "aromatic heterocyclic rings" include 5- or 6-membered aromatic heterocyclic rings, and specific examples include a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, and a triazine ring.

In the present specification, unless otherwise specified, other examples of the "aromatic heterocyclic rings" include a condensed ring of one or more 5- or 6-membered aromatic heterocyclic rings and one or more aromatic carbon rings.

In the present specification, unless otherwise specified, other examples of the "aromatic heterocyclic rings" include a condensed ring of one or more 5- or 6-membered aromatic heterocyclic rings and one or more aromatic carbon rings.

In the present specification, the "organic group" refers to a group containing one or more carbon atoms (or a group formed by removing one hydrogen atom from an organic compound).

Examples of the "organic group" may include:
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents,
a heteroaryl group optionally having one or more substituents,
a cyano group,
an aldehyde group,
$R^r O—$,
$R^r CO—$,
$R^r SO_2—$,
$R^r OCO—$, and
$R^r OSO_2—$
(in these formulas, $R^r$ is independently
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents, or
a heteroaryl group optionally having one or more substituents.)

In the present specification, the "organic group" may be, for example, a hydrocarbon group optionally having one or more substituents, wherein to the hydrocarbon group, one or more moieties selected from the group consisting of —$NR^o$—, =N—, —N=, —O—, —S—, —C(=O)O—, —OC(=O)—, —C(=O)—, —S(=O)—, —S(=O)$_2$—, —S(=O)$_2$—$NR^o$—, —$NR^o$—S(=O)$_2$—, —S(=O)—$NR^o$—, and —$NR^o$—S(=O)— (in these formulas, $R^o$ is independently a hydrogen atom or an organic group) may be inserted.

As is generally understood based on common knowledge in the field of chemistry, examples of the hydrocarbon group with a heteroatom thus inserted may include non-aromatic heterocyclic groups and heteroaryl groups.

In the present specification, the number of carbon atoms in the "hydrocarbon group" of the "hydrocarbon group optionally having one or more substituents" may be, for example, 1 to 100, 1 to 80, 1 to 60, 1 to 40, 1 to 30, 1 to 20, or 1 to 10 (e.g., 1, 2, 3, 4, 5, 6, 7, 8, 9, or 10).

In the present specification, examples of the "substituents" in the "hydrocarbon group optionally having one or more substituents," "alkyl group optionally having one or more substituents," "alkenyl group optionally having one or more substituents," "alkynyl group optionally having one or more substituents," "cycloalkyl group optionally having one or more substituents," "cycloalkenyl group optionally having one or more substituents," "cycloalkadienyl group optionally having one or more substituents," "aryl group optionally having one or more substituents," and "aralkyl group optionally having one or more substituents" may include a halo group, a nitro group, a cyano group, an oxo group, a thioxo group, a sulfo group, a sulfamoyl group, a sulfinamoyl group, and a sulfenamoyl group.

The number of substituents may be in the range of 1 to the maximum substitutable number (e.g., 1, 2, 3, 4, 5, or 6).

In the present specification, examples of the "hydrocarbon group" may include an alkyl group, an alkenyl group, an alkynyl group, a cycloalkyl group, a cycloalkenyl group, a cycloalkadienyl group, an aryl group, an aralkyl group, and a group that is a combination of these groups.

In the present specification, unless otherwise specified, examples of the "alkyl group" may include linear or branched $C_1$-$C_{10}$ alkyl groups, such as methyl, ethyl, propyl, isopropyl, butyl, isobutyl, sec-butyl, tert-butyl, pentyl, isopentyl, neopentyl, hexyl, heptyl, octyl, nonyl, and decyl.

In the present specification, the "fluoroalkyl group" is an alkyl group in which at least one hydrogen atom is replaced by a fluorine atom.

In the present specification, the number of fluorine atoms in the "fluoroalkyl group" may be 1 or more (e.g., 1 to 3, 1 to 6, 1 to 12, or 1 to the maximum substitutable number).

As a person skilled in the art would generally understand, the suffix "perhalogeno" means that all hydrogen atoms are replaced by halo groups.

As a person skilled in the art would generally understand, the suffix "perfluoro" means that all hydrogen atoms are replaced by halo groups.

The "fluoroalkyl group" includes a perfluoroalkyl group.

The "perfluoroalkyl group" is an alkyl group in which all hydrogen atoms are replaced by fluorine atoms. Specific examples of the perfluoroalkyl group include a trifluoromethyl group ($CF_3$—) and a pentafluoroethyl group ($C_2F_5$—).

In the present specification, the "fluoroalkyl group" may be, for example, a fluoroalkyl group having 1 to 20, 1 to 12, 1 to 6, 1 to 4, 1 to 3, 6, 5, 4, 3, 2, or 1 carbon atom.

In the present specification, the "fluoroalkyl group" may be a linear or branched fluoroalkyl group.

In the present specification, specific examples of the "fluoroalkyl group" include a fluoromethyl group, a difluoromethyl group, a trifluoromethyl group ($CF_3$—), a 2,2,2-trifluoroethyl group, a pentafluoroethyl group ($C_2F_5$—), a tetrafluoropropyl group (e.g., $HCF_2CF_2CH_2$—), a hexafluoropropyl group (e.g., $(CF_3)_2CH$—), a nonafluorobutyl group, an octafluoropentyl group (e.g., $HCF_2CF_2CF_2CF_2CH_2$—), a tridecafluorohexyl group, and the like.

In the present specification, unless otherwise specified, examples of the "alkenyl group" may include linear or branched $C_{2-10}$ alkenyl groups, such as vinyl, 1-propen-1-yl, 2-propen-1-yl, isopropenyl, 2-buten-1-yl, 4-penten-1-yl, and 5-hexen-1-yl.

In the present specification, unless otherwise specified, examples of the "alkynyl group" may include linear or branched $C_2$-$C_{10}$ alkynyl groups, such as ethynyl, 1-propyn-1-yl, 2-propyn-1-yl, 4-pentyn-1-yl, and 5-hexyn-1-yl.

In the present specification, unless otherwise specified, examples of the "cycloalkyl group" may include $C_3$-$C_7$ cycloalkyl groups, such as cyclopropyl, cyclobutyl, cyclopentyl, cyclohexyl, and cycloheptyl.

In the present specification, unless otherwise specified, examples of the "cycloalkenyl group" may include $C_3$-$C_7$ cycloalkenyl groups, such as cyclopropenyl, cyclobutenyl, cyclopentenyl, cyclohexenyl, and cycloheptenyl.

In the present specification, unless otherwise specified, examples of the "cycloalkadienyl group" may include $C_4$-$C_{ia}$ cycloalkadienyl groups, such as cyclobutadienyl, cyclopentadienyl, cyclohexadienyl, cycloheptadienyl, cyclooctadienyl, cyclononadienyl, and cyclodecadienyl.

In the present specification, unless otherwise specified, the "aryl group" may be monocyclic, bicyclic, tricyclic, or tetracyclic.

In the present specification, unless otherwise specified, the "aryl group" may be a $C_6$-$C_{18}$ aryl group.

In the present specification, unless otherwise specified, examples of the "aryl group" may include phenyl, 1-naphthyl, 2-naphthyl, 2-biphenyl, 3-biphenyl, 4-biphenyl, and 2-anthryl.

In the present specification, unless otherwise specified, examples of the "aralkyl group" may include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In the present specification, unless otherwise specified, the "non-aromatic heterocyclic group" may be monocyclic, bicyclic, tricyclic, or tetracyclic.

In the present specification, unless otherwise specified, the "non-aromatic heterocyclic group" may be, for example, a non-aromatic heterocyclic group that contains, as a ring-constituting atom(s), 1 to 4 heteroatoms selected from an oxygen atom, a sulfur atom, and a nitrogen atom, in addition to a carbon atom.

In the present specification, unless otherwise specified, the "non-aromatic heterocyclic group" may be saturated or unsaturated.

In the present specification, unless otherwise specified, examples of the "non-aromatic heterocyclic group" may include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like.

In the present specification, unless otherwise specified, examples of the "heteroaryl group" may include monocyclic aromatic heterocyclic groups (e.g., 5- or 6-membered monocyclic aromatic heterocyclic groups) and aromatic condensed heterocyclic groups (e.g., 5- to 18-membered aromatic condensed heterocyclic groups).

In the present specification, unless otherwise specified, examples of the "5- or 6-membered monocyclic aromatic heterocyclic groups" may include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like.

In the present specification, unless otherwise specified, examples of the "5- to 18-membered aromatic condensed heterocyclic groups" may include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like In the present specification, unless otherwise specified, examples of the "substituents" in the "non-aromatic heterocyclic group optionally having one or more substituents" and "heteroaryl group optionally having one or more substituents" may include a hydrocarbon group optionally having one or more substituents, a halo group, a nitro group, a cyano group, an oxo group, a thioxo group, a sulfo group, a sulfamoyl group, a sulfinamoyl group, and a sulfenamoyl group.

The number of substituents may be in the range of 1 to the maximum substitutable number (e.g., 1, 2, 3, 4, 5, or 6).

Step A

The method for producing a fluorinated organic compound according to the present invention comprises step A of fluorinating an organic compound (1) by reaction with a fluorine source (3)

in the presence of a polymer (2ap) having one or more hypervalent iodine aromatic ring moieties, in the presence of a combination of an oxidant (2bo) and a polymer (2bp) having one or more iodine aromatic ring moieties, or in the presence of a polymer (2cp) having one or more $IF_2$-substituted aromatic ring moieties;

wherein the fluorine source (3) is a fluorine source (3a) represented by formula: $MF_n$, wherein M is H, a metal of Group 1 of the periodic table, or a metal of Group 2 of the periodic table; and n is 1 or 2;

the iodine-containing polymer (2cp) having one or more $IF_2$-substituted aromatic ring moieties; or a combination thereof.

In order to distinguish the organic compound, which is the substrate of the production method of the present invention, and the fluorinated organic compound, which is the target product of the production method of the present invention, the former is also referred to as the "organic compound," and the latter is also referred to as the "fluorinated organic compound," in the present specification.

Substrate: Organic Compound (1) and Product: Fluorinated Organic Compound

The organic compound (1), which is the substrate of the production method of the present invention, may be preferably a carbonyl compound having a hydrogen atom (1a), or a compound having one or more unsaturated carbon-carbon bonds.

Just for the sake of confirmation, the organic compound (1) may have one or more fluorine atoms.

Preferable examples of the organic compound (1) include:

a compound represented by formula (1a) (also referred to as "the organic compound (1a) in the present specification"):

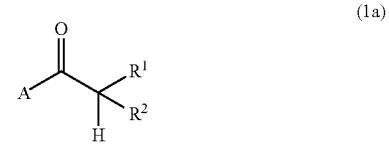

(1a)

wherein

A is a hydrogen atom, an aromatic group optionally having one or more substituents, an alkyl group optionally having one or more substituents, a halogen atom, —OR, or —NR$_2$, $R^1$ is a hydrogen atom, an organic group, or a halogen atom, $R^2$ is a hydrogen atom, an organic group, or a halogen atom, and R is independently at each occurrence a hydrogen atom or an organic group;

a compound represented by formula (1b) (also referred to as "the organic compound (1b) in the present specification"):

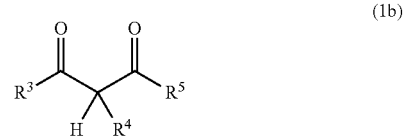

(1b)

wherein
R³ is a hydrogen atom, an aromatic group optionally having one or more substituents, an alkyl group optionally having one or more substituents, a halogen atom, —OR, or —NR₂,
R⁴ is a hydrogen atom, an aromatic group optionally having one or more substituents, an alkyl group optionally having one or more substituents, a halogen atom, —OR, or —NR₂,
R⁵ is a hydrogen atom, an aromatic group optionally having one or more substituents, an alkyl group optionally having one or more substituents, a halogen atom, —OR, or —NR₂, and
R is independently at each occurrence a hydrogen atom or an organic group; or a compound represented by formula (1c) (also referred to as "the organic compound (1c) in the present specification"):

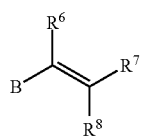

(1c)

wherein
B is an aromatic group optionally having one or more substituents, or an alkyl group optionally having one or more substituents,
R⁶ is a hydrogen atom, an organic group, or a halogen atom,
R⁷ is a hydrogen atom, an organic group, or a halogen atom, and
R⁸ is a hydrogen atom, an organic group, or a halogen atom.

In the organic compound (1a), preferably, for example,
A is an aromatic group optionally having one or more substituents,
R¹ is a hydrogen atom or a $C_1$-$C_5$ alkyl group optionally having one or more substituents, and
R² is a hydrogen atom or a $C_1$-$C_5$ alkyl group optionally having one or more substituents.

In the organic compound (1b), preferably, for example,
R³ is an aromatic group optionally having one or more substituents, an alkyl group optionally having one or more substituents, —OR, or —NR₂,
R⁴ is a hydrogen atom, a halogen atom, —OR, or —NR₂,
R⁵ is an aromatic group optionally having one or more substituents, an alkyl group optionally having one or more substituents, —OR, or —NR₂, and
R is independently at each occurrence a hydrogen atom or an organic group.

In the organic compound (1c), preferably, for example,
B is an aromatic group optionally having one or more substituents,
R⁶ is a hydrogen atom or a $C_1$-$C_5$ alkyl group,
R⁷ is a hydrogen atom or a $C_1$-$C_5$ alkyl group, and
R⁸ is a hydrogen atom or a $C_1$-$C_5$ alkyl group.

By the production method of the present invention, a fluorinated organic compound (1af) of the following formula is obtained corresponding to the organic compound (1a).

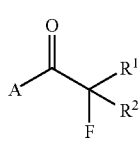

(1af)

(The symbols in the formula are the same as those in formula (1a).)

By the production method of the present invention, a fluorinated organic compound (1bf) of the following formula is obtained corresponding to the organic compound (1b).

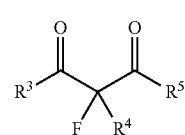

(1bf)

(The symbols in the formula are the same as those in the formula (1b).)

By the production method of the present invention, a fluorinated organic compound (1cf) of the following formula is obtained corresponding to the organic compound (1c).

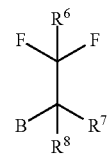

(1cf)

(The symbols in the formula are the same as those in the formula (1c).)

Polymers and Oxidant
Step A Uses:
a polymer having one or more hypervalent iodine aromatic ring moieties (in the present specification, this polymer is also referred to as "the hypervalent iodine aromatic ring-containing polymer (2ap)" or simply "the polymer (2ap)");
a combination of an oxidant (2bo) and a polymer having one or more iodine aromatic ring moieties (in the present specification, this polymer is also referred to as "the iodine aromatic ring-containing polymer (2bp)" or simply "the polymer (2bp)"); or
an iodine-containing polymer having one or more IF₂-substituted aromatic ring moieties (in the present specification, this polymer is also referred to as "the IF₂-substituted aromatic ring-containing polymer (2cp)" or simply "the polymer (2cp)").
Oxidant (2bo)
In step A, the hypervalent iodine aromatic ring-containing polymer (2ap) can be preferably used in the absence of an oxidant.
The phrase "in the absence of an oxidant" as mentioned herein may mean that the amount of oxidant in the reaction system of step A is 0.1 mol or less per mol of the organic compound (1).
In step A, the iodine aromatic ring-containing polymer (2bp) is used together with the oxidant (2bo).
Examples, preferable examples, and more preferable examples of the oxidant (2bo) include those of an oxidant (C) described in step C below.
The amount of the oxidant (2bo) used in step A may be generally in the range of 0.1 to 20 mol per mol of the organic compound (1).
Polymer (2ap), Polymer (2bp), and Polymer (2cp)
In the above polymers, one or more hypervalent iodine aromatic ring moieties, one or more iodine aromatic ring moieties, or one or more IF$_2$-substituted aromatic ring moieties can be present in the main chain, a side chain, or a pendant group, or as a side chain itself, or as a pendant group itself.

The hypervalent iodine aromatic ring-containing polymer (2ap) may be, for example, a polymer containing one or more members selected from the group consisting of —CH—CR—, —CR—C—, —CR—R—, —R—, —CO—O—, —O—CO—, —CO—NR—, —NR—CO—, —O—, —CO—, —S—, and —SO— (in these formulas, R is a hydrogen atom or an organic group), and one or more structural units (provided that the polymer has one or more hypervalent iodine aromatic rings in one or more R moieties).

The iodine aromatic ring-containing polymer (2bp) may be, for example, a polymer containing one or more members selected from the group consisting of —CH—CR—, —CR—C—, —CR—R—, —R—, —CO—O—, —O—CO—, —CO—NR—, —NR—CO—, —O—, —CO—, —S—, and —SO— (in these formulas, R is a hydrogen atom or an organic group), and one or more structural units (provided that this polymer has one or more iodine aromatic rings in one or more R moieties).

The IF$_2$-substituted aromatic ring-containing polymer (2cp) may be, for example, a polymer containing one or more members selected from the group consisting of —CH—CR—, —CR—C—, —CR—R—, —R—, —CO—O—, —O—CO—, —CO—NR—, —NR—CO—, —O—, —CO—, —S—, and —SO— (in these formulas, R is a hydrogen atom or an organic group), and one or more structural units (provided that this polymer has one or more iodine aromatic rings in one or more R moieties).

The hypervalent iodine aromatic ring-containing polymer (2ap) may be, for example, polystyrene, polyester, polyamide, polyether, polycarbonate, or polythioether (preferably polystyrene), each of which has one or more hypervalent iodine aromatic ring moieties.

The iodine aromatic ring-containing polymer (2bp) may be, for example, polystyrene, polyester, polyamide, polyether, polycarbonate, or polythioether (preferably polystyrene), each of which has one or more iodine aromatic ring moieties.

The IF$_2$-substituted aromatic ring-containing polymer (2cp) may be, for example, polystyrene, polyester, polyamide, polyether, polycarbonate, or polythioether (preferably polystyrene), each of which has one or more IF$_2$-substituted aromatic ring moieties.

Just for the sake of confirmation, the aromatic ring may be an aromatic ring that is essential for the name of the polymer (e.g., benzene ring in polystyrene).

The hypervalent iodine aromatic ring moiety in the hypervalent iodine aromatic ring-containing polymer (2ap) is preferably a hypervalent iodine aromatic ring moiety represented by formula (2ap1):

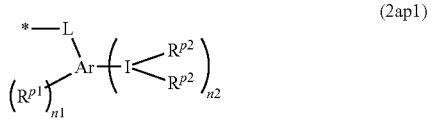

wherein
Ar is an aromatic ring,
R$^{p1}$ is independently at each occurrence
  an alkyl group,
  an alkoxy group,
  a group: —O—(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
  a group: —(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
  a halogen atom,
  a cyano group,
  a nitro group,
  a carboxylic acid group, or
  a sulfonic acid group;
R$^{p2}$ is independently at each occurrence
  an alkyl group,
  an alkoxy group,
  a group: —O—(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
  a group: —(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
  a halogen atom,
  a cyano group,
  a nitro group,
  a carboxylic acid group,
  a sulfonic acid group,
  a hydroxy group, or
  a phosphoryloxy group; or
two R$^{p2}$ bonded to one iodine atom optionally together form =O;
n1 is a number greater than or equal to 0;
n2 is a number greater than or equal to 1;
the sum of n1 and n2 is in the range of 1 to 11;
L is a bond or a linker; and
* is a binding site.

In the formula, Ar is preferably a benzene ring.

The iodine aromatic ring moiety in the hypervalent iodine aromatic ring-containing polymer (2bp) is preferably an iodine aromatic ring moiety represented by formula (2bp1):

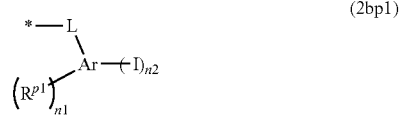

wherein
Ar is an aromatic ring;
R$^{p1}$ is independently at each occurrence
  an alkyl group,
  an alkoxy group,
  a group: —O—(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
  a group: —(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group,
  a halogen atom,
  a cyano group, a nitro group,
a carboxylic acid group, or
a sulfonic acid group;
n1 is a number greater than or equal to 0;
n2 is a number greater than or equal to 1;
the sum of n1 and n2 is in the range of 1 to 11;
L is a bond or a linker; and
* is a binding site.

In the formula, Ar is a benzene ring.

The $IF_2$-substituted aromatic ring moiety in the $IF_2$-substituted aromatic ring moiety-containing polymer (2cp) is preferably an iodine aromatic ring moiety represented by formula (2cp1):

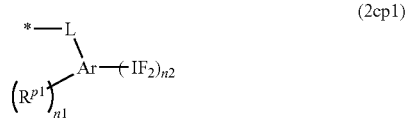

(2cp1)

wherein
Ar is an aromatic ring;
$R^{p1}$ is independently at each occurrence
an alkyl group,
an alkoxy group,
a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a group: —$(CH_2)_q$—$NR_3X$, wherein q is a number greater than or equal to 1; R is H or a $C_1$-$C_2$ alkyl group; and X is a halogen atom, an arylsulfonyloxy group, or an alkylsulfonyloxy group,
a halogen atom,
a cyano group,
a nitro group,
a carboxylic acid group, or
a sulfonic acid group;
n1 is a number greater than or equal to 0;
n2 is a number greater than or equal to 1;
the sum of n1 and n2 is in the range of 1 to 11; and
* is a binding site.

Just for the sake of confirmation, the phrase "each occurrence" as mentioned herein is used with the intention of including not only each occurrence in one formula, but also each occurrence in each of the hypervalent iodine aromatic ring moieties possessed by a plurality of repeating units of the polymer.

The molecular weight of each polymer molecule may be, for example, in the range of 500 to 1000000.

The chain length of the main chain of the linker represented by symbol L in each formula may be, for example, 1 to 100, 1 to 70, 1 to 50, 1 to 30, 1 to 20, or 1 to 10.

Examples of the linker represented by L include alkanediyl, to which one or more (e.g., 1 or 2, 3 to 5, or 6 to 10) divalent groups selected from the group consisting of:
(1) a divalent heteroatom-containing group,
(2) a 1,2-ethenediyl group optionally having one or more substituents (e.g., an alkyl group), and
(3) 1,2-ethindiyl
may be inserted.

Examples of the "divalent heteroatom-containing group" include —O—, —CO—, —$CO_2$—, —S—, —SO—, —$SO_2$—, —$SO_3$—, —$N_2$—, and an imino group, which optionally has one substituent (e.g., an alkyl group).

Each of the polymer organic compounds preferably contains 10 mass % or more of the moiety represented by formula (p1), and has a mass average molecular weight in the range of 500 to 1000000, 500 to 100000, 500 to 10000, or 500 to 1000.

$R^{p1}$ is preferably independently at each occurrence hydrogen, an alkyl group, a cycloalkyl group, an alkoxy group, a halogen atom, a cyano group, a nitro group, a carboxylic acid group, or a sulfonic acid group.

$R^{p2}$ is preferably independently at each occurrence a halogen atom, an acetic acid group, a trifluoroacetic acid group, a tosic acid group, a hydroxy group, a phosphoryloxy group, a trifluoromethanesulfonic acid group, a propionic acid group, a 3,3,3-trifluoropropionic acid group, a perfluoropropionic acid group, a perfluorobutyric acid group, or a methanesulfonic acid group.

A group name using a compound name, such as the "acetic acid group," refers to a group derived from the compound, and in the present specification, it particularly refers to a group derived from the compound and capable of binding to hypervalent iodine.

The polymers (2ap), (2bp), and (2cp) can each be produced according to a known production method.

Fluorine Source (3)

The fluorine source (3) used in step A may be:
a fluorine source (3a) represented by formula: $M^1F_n$, wherein $M^1$ is H, a metal of Group 1 of the periodic table, or a metal of Group 2 of the periodic table; and n is 1 or 2,
the polymer (2cp), or
a combination thereof.

That is, when the $IF_2$-substituted aromatic ring-containing polymer (2cp) is used, the polymer (2cp) can also serve as the fluorine source (3).

$M^1$ may be preferably H, Li, Na, K, Ca, or Cs; more preferably H, Na, K, or Ca; and even more preferably H.

The fluorine source may be preferably a hydrogen fluoride source.

Examples of the fluorine source include anhydrous hydrofluoric acid, a hydrofluoric acid aqueous solution (e.g., a hydrofluoric acid aqueous solution with a concentration of 10 to 70 wt %), and a mixture of hydrofluoric acid, an organic base, and an inorganic base.

In this mixture, the hydrofluoric acid and organic base may be specifically, for example, salts, such as hydrogen fluoride-triethylamine salt [$Et_3N.nHF$ (n=1 to 5)], hydrogen fluoride-pyridine salt [Py.nHF (n=1 to 10)], and hydrogen fluoride-tetraethylammonium fluoride salt [$Et_4NF.nHF$ (n=1 to 10)]; or may be derived therefrom.

In this mixture, the hydrofluoric acid and inorganic base may be specifically, for example, HF—KF($KHF_2$), or may be derived therefrom.

These fluorine sources can be used singly or in combination of two or more.

The amount of fluorine source used may be, for example, as hydrogen fluoride, generally in the range of 0.5 to 100 mol, preferably in the range of 1 to 50 mol, more preferably in the range of 2 to 30 mol, and even more preferably in the range of 3 to 25 mol, per mol of the organic compound, which is the substrate of the production method of the present invention.

The substrate of step A may be added to the reaction system of step A all at once, in several batches, or continuously.

The reaction of step A can be carried out in the presence or absence of a solvent.

The solvent may be a non-polar solvent or a polar solvent.

Examples of the solvent include esters, ketones, aromatic compounds, alcohols, ethers, amines, nitrogen-containing polar organic compounds, nitriles, halogenated hydrocarbons, aliphatic hydrocarbons, fluorine-based solvents, carbonates, other solvents, and combinations thereof.

Examples of esters as the solvent include ethyl acetate, butyl acetate, amyl acetate, ethylene glycol monomethyl ether acetate, and propylene glycol monomethyl ether acetate; and preferably ethyl acetate.

Examples of ketones as the solvent include acetone, methyl ethyl ketone, diethyl ketone, hexanone, methyl isobutyl ketone, heptanone, diisobutyl ketone, acetonylacetone, methylhexanone, acetophenone, cyclohexanone, and diacetone alcohol; and preferably acetone.

Examples of aromatic compounds as the solvent include anisole, benzene, toluene, xylene, and ethylbenzene; and preferably benzene and toluene.

Examples of alcohols as the solvent include methanol, ethanol, n-propanol, isopropanol, n-butanol, pentanol, hexanol, ethylene glycol, diethylene glycol, triethylene glycol, tetraethylene glycol, polyethylene glycol, propylene glycol, dipropylene glycol, tripropylene glycol, polypropylene glycol, trimethylene glycol, and hexanetriol; and preferably methanol and ethanol.

Examples of ethers as the solvent include diethyl ether, dibutyl ether, tetrahydrofuran, tetrahydropyran, dioxane, dimethoxyethane, diethylene glycol diethyl ether, ethylene glycol monomethyl ether, ethylene glycol monoethyl ether, diethylene glycol monomethyl ether, diethylene glycol monoethyl ether, propylene glycol monomethyl ether (PGME; also known as "1-methoxy-2-propanol"), propylene glycol monoethyl ether, triethylene glycol dimethyl ether, triethylene glycol diethyl ether, tetraethylene glycol dimethyl ether, and tetraethylene glycol diethyl ether; and preferably diethyl ether and tetrahydrofuran.

Examples of amines as the solvent include monoethanolamine, diethanolamine, and triethanolamine.

Examples of nitrogen-containing polar organic compounds as the solvent include N,N-dimethylformamide, N,N-dimethylacetamide, N-methyl-2-pyrrolidone, 2-pyrrolidone, and 1,3-dimethyl-2-imidazolidinone; and preferably N,N-dimethylformamide, N,N-dimethylacetamide, and N-methyl-2-pyrrolidone.

Examples of nitriles as the solvent include acetonitrile, propionitrile, butyronitrile, isobutyronitrile, benzonitrile, and adiponitrile; and preferably acetonitrile.

Examples of halogenated hydrocarbons as the solvent include dichloromethane, dichloroethane, chloroform, carbon tetrachloride, tetrachloroethane, trichloroethane, chlorobenzene, dichlorobenzene, and chlorotoluene; and preferably dichloromethane and chloroform.

Examples of aliphatic hydrocarbons as the solvent include hexane, cyclohexane, heptane, octane, nonane, decane, undecane, dodecane, and mineral spirits; and preferably cyclohexane and heptane.

Examples of fluorine-based solvents include perfluorobenzene, trifluorotoluene, ditrifluorobenzene, and trifluoroethanol; and preferably perfluorobenzene and trifluoroethanol.

Examples of carbonates as the solvent include tetralin dimethyl carbonate, methyl ethyl carbonate, diethyl carbonate, ethylene carbonate, and propylene carbonate; and preferably ethylene carbonate and propylene carbonate.

Examples of other solvents include acetic acid, pyridine, dimethylsulfoxide, sulfolane, and water.

These solvents can be used singly or in combination of two or more.

The amount of solvent used may be, for example, generally in the range of 0 to 200 parts by mass, preferably in the range of 0 to 100 parts by mass, and more preferably in the range of 0 to 50 parts by mass, per part by mass of the organic compound, which is the substrate of the production method of the present invention.

The temperature of step A may be generally in the range of −78 to 200° C., preferably in the range of −10 to 100° C., and more preferably in the range of 0 to 100° C.

The time of step A may be generally in the range of 0.1 to 72 hours, preferably in the range of 0.1 to 48 hours, more preferably in the range of 0.1 to 36 hours, and even more preferably in the range of 0.1 to 24 hours.

Step B

In the method of the present invention, after step A is started, the hypervalent iodine aromatic ring moiety in the polymer (2bp) is preferably changed to an iodine aromatic ring moiety.

The method of the present invention preferably comprises step B of separating the polymer (2ap), the polymer (2bp), or the polymer (2cp) (preferably the polymer (2ap)) from the reaction liquid after step A is started.

The separation may be generally performed after the start of step A, and is not necessarily performed after the reaction of step A is completely completed.

The separation can be preferably achieved by separating the polymer, which is a solid, from the production liquid and/or reaction liquid, which are liquids, depending on the difference in their forms.

As a means for the separation, for example, a conventional method such as filtration can be used.

The conditions of step B may be set as appropriate based on common technical knowledge.

Step C

The method of the present invention preferably comprises step C of oxidizing the polymer (preferably the polymer (2ap)) separated from the reaction liquid in step B with an oxidant (C).

The polymer to be subjected to step C may be subjected to other steps (e.g., washing) after the separation.

The polymer oxidized in step C can be used in step A.

The oxidant (C) may be preferably, for example, one or more members selected from the group consisting of:

(i) a compound represented by formula: $R^X COOOM^{2a}$ wherein $R^X$ is a hydrocarbon group optionally having one or more substituents, and $M^2$ is a hydrogen atom or a metal atom;

(ii) a compound represented by formula: $R^X OOM^{2b}$ wherein $R^X$ is a hydrogen atom or a hydrocarbon group optionally having one or more substituents, and $M^2$ is a hydrogen atom or a metal atom; and (iii) a metal oxide.

Examples of the oxidant (C) include metachloroperbenzoic acid, hydrogen peroxide, peracetic acid, perbenzoic acid, tert-butyl hydroperoxide, cumene hydroperoxide, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

Preferable examples of the oxidant (C) include metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

More preferable examples of the oxidant (C) include metachloroperbenzoic acid.

These can be used singly or in combination of two or more.

The amount of oxidant used in step C may be generally in the range of 0.1 to 100 parts by mass, preferably in the range of 0.4 to 50 parts by mass, and more preferably in the range of 0.6 to 20 parts by mass, per part by mass of the polymer.

The conditions of step C may be set as appropriate based on common technical knowledge.

The target fluorinated organic compound obtained in this manner can be isolated or purified, if desired, by a conventional method, such as filtration, extraction, dissolution, concentration, precipitation, dehydration, adsorption, or chromatography, or a combination of these methods.

EXAMPLES

The present invention is described in more detail below with reference to Examples; however, the present invention is not limited thereto.

The meanings of the symbols and abbreviations in the Examples are shown below.
Py: pyridine Example 1 (synthesis 1 of ethyl 2-fluoro-3-oxo-3-phenylpropanoate)

Ethyl 3-oxo-3-phenylpropanoate (0.2 mmol), poly[4-(diacetoxyiodo)styrene] (1.2 eq.), dichloromethane (1 ml), and Py.HF (10 eq. HF) were mixed, and heated and stirred at 40° C. for 1 hour. The reaction liquid was analyzed by F-NMR, and it was confirmed that the title target product was obtained in a yield of 4%.

On the other hand, the reaction product liquid was filtered to recover a polymer derived from the above polymer in a recovery amount of 90% (in terms of mol).

Example 2 (synthesis 2 of ethyl 2-fluoro-3-oxo-3-phenylpropanoate)

A target product was synthesized in the same manner as in Example 1, except that the amount of poly[4-(diacetoxyiodo)styrene] was changed to 2.0 eq., dichloromethane was changed to toluene, Py.HF was changed to Et3N.5HF, and the reaction time was extended to 2 days. It was confirmed that the title target product was obtained in a yield of 15%.

On the other hand, the reaction product liquid was filtered to recover a polymer derived from the above polymer in a recovery amount of 90% (in terms of mol).

Example 3 (synthesis 1 of ethyl 2-fluoro-3-oxoheptanoate)

Ethyl 3-oxoheptanoate (0.2 mmol), poly[4-(diacetoxyiodo)styrene] (1.2 eq.), dichloromethane (1 ml), and Py.HF (10 eq. HF) were mixed, and heated and stirred at 40° C. for 17 hours. The reaction liquid was analyzed by F-NMR, and it was confirmed that the title target product was obtained in a yield of 9%.

On the other hand, the reaction product liquid was filtered to recover a polymer derived from the above polymer in a recovery amount of 90% (in terms of mol).

The invention claimed is:
1. A method for producing a fluorinated organic compound, comprising:
step A of fluorinating an organic compound (1) by reaction with a fluorine source (3) in the presence of an iodine-containing polymer (2ap) having one or more hypervalent iodine aromatic ring moieties, or
in the presence of a combination of an oxidant (2bo) and an iodine-containing polymer (2 bp) having one or more iodine aromatic ring moieties, or
in the presence of an iodine-containing polymer (2cp) having one or more $IF_2$-substituted aromatic ring moieties;
wherein the organic compound (1) is:
an organic compound represented by formula (1a):

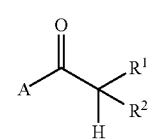

(1a)

wherein
A is a hydrogen atom, an aromatic group optionally having one or more substituents, an alkyl group optionally having one or more substituents, a halogen atom, —OR, or —$NR_2$, wherein the substituents are a halo group, a nitro group, a cyano group, an oxo group, a thioxo group, a sulfo group, a sulfamoyl group, a sulfinamoyl group, or a sulfenamoyl group,
$R^1$ is a hydrogen atom, an organic group, or a halogen atom,
$R^2$ is a hydrogen atom, an organic group, or a halogen atom, and
R is independently at each occurrence a hydrogen atom or an organic group, or
an organic compound represented by formula (1b):

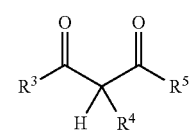

(1b)

wherein
$R^3$ is a hydrogen atom, an aromatic group optionally having one or more substituents, an alkyl group optionally having one or more substituents, a halogen atom, —OR, or —$NR_2$, wherein the substituents are a halo group, a nitro group, a cyano group, an oxo group, a thioxo group, a sulfo group, a sulfamoyl group, a sulfinamoyl group, or a sulfenamoyl group,
$R^4$ is a hydrogen atom, an aromatic group optionally having one or more substituents, an alkyl group optionally having one or more substituents, a halogen atom, —OR, or —$NR_2$, wherein the substituents are a halo group, a nitro group, a cyano group, an oxo group, a thioxo group, a sulfo group, a sulfamoyl group, a sulfinamoyl group, or a sulfenamoyl group,
$R^5$ is a hydrogen atom, an aromatic group optionally having one or more substituents, an alkyl group optionally having one or more substituents, a halogen atom, —OR, or —$NR_2$, wherein the substituents are a halo group, a nitro group, a cyano group, an oxo group, a thioxo group, a sulfo group, a sulfamoyl group, a sulfinamoyl group, or a sulfenamoyl group, and
R is independently at each occurrence a hydrogen atom or an organic group;

wherein the fluorinated organic compound is:
a fluorinated organic compound (1af) represented by formula (1af):
wherein A, $R^1$ and $R^2$ are the same as those defined in formula (1a) above, or
a fluorinated organic compound (1bf) represented by formula (1bf):
wherein $R^3$, $R^4$ and $R^5$ are the same as those defined in formula (1b) above;
wherein the fluorine source (3) is a mixture of hydrofluoric acid and an organic base;
wherein the polymer (2ap) having one or more hypervalent iodine aromatic ring moieties is a polymer having one or more hypervalent iodine aromatic ring moieties represented by formula (2a1):

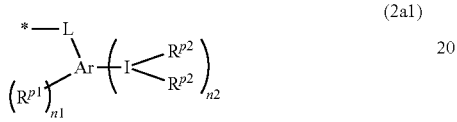
(2a1)

wherein in formula (2a1),
Ar is an aromatic ring,
$R^{p1}$ is independently at each occurrence
an alkyl group,
an alkoxy group,
a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a halogen atom,
a cyano group,
a nitro group,
a carboxylic acid group, or
a sulfonic acid group;
$R^{p2}$ is independently at each occurrence
an alkyl group,
an alkoxy group,
a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a halogen atom,
a cyano group,
a nitro group,
a carboxylic acid group,
a sulfonic acid group,
a hydroxy group, or
a phosphoryloxy group; or
two $R^{p2}$ bonded to one iodine atom optionally together form =O;
n1 is a number greater than or equal to 0;
n2 is a number greater than or equal to 1;
the sum of n1 and n2 is in the range of 1 to 11;
L is a bond or a linker, wherein the linker is an alkanediyl to which one or more divalent groups selected from the group consisting of (1) a divalent heteroatom-containing group, (2) a 1,2-ethenediyl group optionally having one or more alkyl groups, and (3) 1,2-ethindiyl, may be inserted, and a chain length of the main chain of the linker is 1 to 100; and
* is a binding site;
wherein the polymer (2 bp) having one or more iodine aromatic ring moieties is a polymer having one or more iodine aromatic ring moieties represented by formula (2bp1):

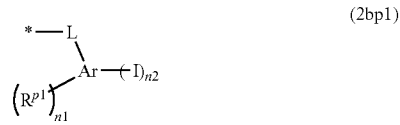
(2bp1)

wherein in formula (2bp1),
Ar is an aromatic ring;
$R^{p1}$ is independently at each occurrence
an alkyl group,
an alkoxy group,
a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a halogen atom,
a cyano group,
a nitro group,
a carboxylic acid group, or
a sulfonic acid group;
n1 is a number greater than or equal to 0;
n2 is a number greater than or equal to 1;
the sum of n1 and n2 is in the range of 1 to 11;
L is a bond or a linker, wherein the linker is an alkanediyl to which one or more divalent groups selected from the group consisting of (1) a divalent heteroatom-containing group, (2) a 1,2-ethenediyl group optionally having one or more alkyl groups, and (3) 1,2-ethindiyl, may be inserted, and a chain length of the main chain of the linker is 1 to 100; and
* is the binding site; and
wherein the iodine-containing polymer (2cp) having one or more $IF_2$-substituted aromatic ring moieties is a polymer having one or more $IF_2$-substituted aromatic ring moieties represented by formula (2cp1):

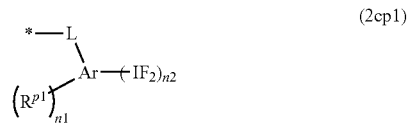
(2cp1)

wherein in formula (2cp1),
Ar is an aromatic ring;
substituent $R^{p1}$ is independently at each occurrence an alkyl group, an alkoxy group, a halogen atom, a cyano group, a nitro group, a carboxylic acid group, or a sulfonic acid group;

n1 is a number greater than or equal to 0;

n2 is an integer of 1 to 5;

L is a bond or a linker, wherein the linker is an alkanediyl to which one or more divalent groups selected from the group consisting of (1) a divalent heteroatom-containing group, (2) a 1,2-ethenediyl group optionally having one or more alkyl groups, and (3) 1,2-ethindiyl, may be inserted, and a chain length of the main chain of the linker is 1 to 100; and

* is a binding site.

2. The production method according to claim 1, wherein in step A, the organic compound (1) is fluorinated by reaction with the fluorine source (3) in the presence of the polymer (2ap).

3. The production method according to claim 1, wherein Ar in the formula (2a1) is a benzene ring.

4. The production method according to claim 1, wherein $R^{p1}$ in the formula (2a1) is independently at each occurrence an alkyl group, an alkoxy group, or a halogen atom.

5. The production method according to claim 1, wherein $R^{p2}$ in the formula (2a1) is independently at each occurrence a halogen atom, an acetic acid group, a trifluoroacetic acid group, a tosic acid group, a hydroxy group, a phosphoryloxy group, a trifluoromethanesulfonic acid group, a propionic acid group, a 3,3,3-trifluoropropionic acid group, a perfluoropropionic acid group, a perfluorobutyric acid group, or a methanesulfonic acid group.

6. The production method according to claim 1, wherein the polymer (2ap) contains 1 mass % or more of the moiety represented by formula (2a1), and has a mass average molecular weight in the range of 500 to 1000000.

7. The production method according to claim 1, wherein in step A, the organic compound (1) is fluorinated by reaction with the fluorine source (3) in the presence of the combination of the polymer (2 bp) and the oxidant (2bo).

8. The production method according to claim 1, wherein Ar in the formula (2bp1) is a benzene ring.

9. The method according to claim 1, wherein $R^{p1}$ in the formula (2bp1) is independently at each occurrence an alkyl group, an alkoxy group, or a halogen atom.

10. The production method according to claim 1, wherein the polymer (2 bp) contains 1 mass % or more of the moiety represented by formula (2bp1), and has a mass average molecular weight in the range of 500 to 1000000.

11. The production method according to claim 1, wherein the oxidant (2bo) is one or more members selected from the group consisting of:

(i) a compound represented by formula: $R^X COOOM$, wherein $R^X$ is a hydrocarbon group optionally having one or more substituents, and M is a hydrogen atom or a metal atom;

(ii) a compound represented by formula: $R^X OOM$, wherein $R^X$ is a hydrogen atom or a hydrocarbon group optionally having one or more substituents, and M is a hydrogen atom or a metal atom; and (iii) a metal oxide.

12. The production method according to claim 11, wherein the oxidant (2bo) is one or more members selected from the group consisting of metachloroperbenzoic acid, hydrogen peroxide, peracetic acid, perbenzoic acid, tert-butyl hydroperoxide, cumene hydroperoxide, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

13. The production method according to claim 1, wherein in step A, the organic compound (1) is fluorinated by reaction with the iodine-containing polymer (2cp) having one or more $IF_2$-substituted aromatic ring moieties.

14. The production method according to claim 1, wherein Ar in the formula (2cp1) is a benzene ring.

15. The method according to claim 1, wherein $R^{p1}$ in the formula (2cp1) is independently at each occurrence an alkyl group, an alkoxy group, or a halogen atom.

16. The production method according to claim 1, wherein the iodine-containing polymer (2cp) having one or more $IF_2$-substituted aromatic ring moieties contains 1 mass % or more of the moiety represented by formula (2cp1), and has a mass average molecular weight in the range of 500 to 1000000.

17. The method according to claim 1, further comprising step B of separating the polymer (2ap), the polymer (2 bp), or the polymer (2cp) from a reaction liquid after step A is started.

18. The method according to claim 17, further comprising step C of oxidizing the polymer (2ap), the polymer (2 bp), or the polymer (2cp) separated from the reaction liquid in step B with an oxidant (C).

19. The production method according to claim 18, wherein the oxidant (C) is one or more members selected from the group consisting of metachloroperbenzoic acid, hydrogen peroxide, peracetic acid, perbenzoic acid, tert-butyl hydroperoxide, cumene hydroperoxide, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

20. The method according to claim 19, wherein the oxidant (C) is one or more members selected from the group consisting of metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

* * * * *